United States Patent [19]
Bartl et al.

[11] 4,301,028
[45] Nov. 17, 1981

[54] CONTROL REAGENT FOR HEPARIN ACTIVITY DETERMINATION

[75] Inventors: Knut Bartl, Tutzing; Joachim Ziegenhorn, Starnberg; Peter Wunderwald, Haunshofen; Klaus Beaucamp, Tutzing; Helmut Lill, Wielenbach, all of Fed. Rep. of Germany

[73] Assignee: Boehringer Mannheim GmbH, Mannheim-Waldhof, Fed. Rep. of Germany

[21] Appl. No.: 110,581

[22] Filed: Jan. 9, 1980

[30] Foreign Application Priority Data

Jan. 31, 1979 [DE] Fed. Rep. of Germany ....... 2903701

[51] Int. Cl.³ .................... G01N 33/16; C09K 3/00
[52] U.S. Cl. .................... 252/408; 23/230 B; 23/918; 424/2; 424/3; 424/183; 435/13
[58] Field of Search .............. 252/408; 23/230 B, 918; 424/2, 3, 183; 435/4, 13

[56] References Cited

U.S. PATENT DOCUMENTS

| 3,030,272 | 4/1962 | Schultz | 424/183 |
|---|---|---|---|
| 3,985,618 | 10/1976 | Innerfield | 435/13 |
| 4,056,484 | 11/1977 | Heimburger et al. | 252/408 |
| 4,067,777 | 1/1978 | Innerfield et al. | 435/13 |
| 4,090,977 | 5/1978 | Dubin | 252/408 |
| 4,106,990 | 8/1978 | Karges et al. | 435/13 |
| 4,127,502 | 11/1978 | Limutti et al. | 252/408 |
| 4,195,072 | 3/1980 | Workman, Jr. | 252/408 |
| 4,216,117 | 8/1980 | Proksch et al. | 252/408 |
| 4,234,682 | 11/1980 | Bartl et al. | 435/13 |

FOREIGN PATENT DOCUMENTS 2812943 10/1979 Fed. Rep. of Germany ...... 252/408

OTHER PUBLICATIONS

Chesterman, C. N. et al., Brit. J. Haematology, vol. 40, pp. 489–500 (1978).

Primary Examiner—Teddy S. Gron
Attorney, Agent, or Firm—Sprung, Felfe, Horn, Lynch & Kramer

[57] ABSTRACT

A control reagent for heparin activity determination comprising
  20 to 1500 USP heparin,
  2000 to 30000 IU antithrombin III,
  0.15 to 1.5 millimoles serum albumin,
  0.005 to 0.05 mole ethylenediaminetetraacetic acid sodium salt,
  0 to 0.4 mole saccharose,
  2000 to 20000 U aprotinin, and
  buffer substance, pH 6.5 to 7.5,
per liter of control reagent solution.

4 Claims, 1 Drawing Figure

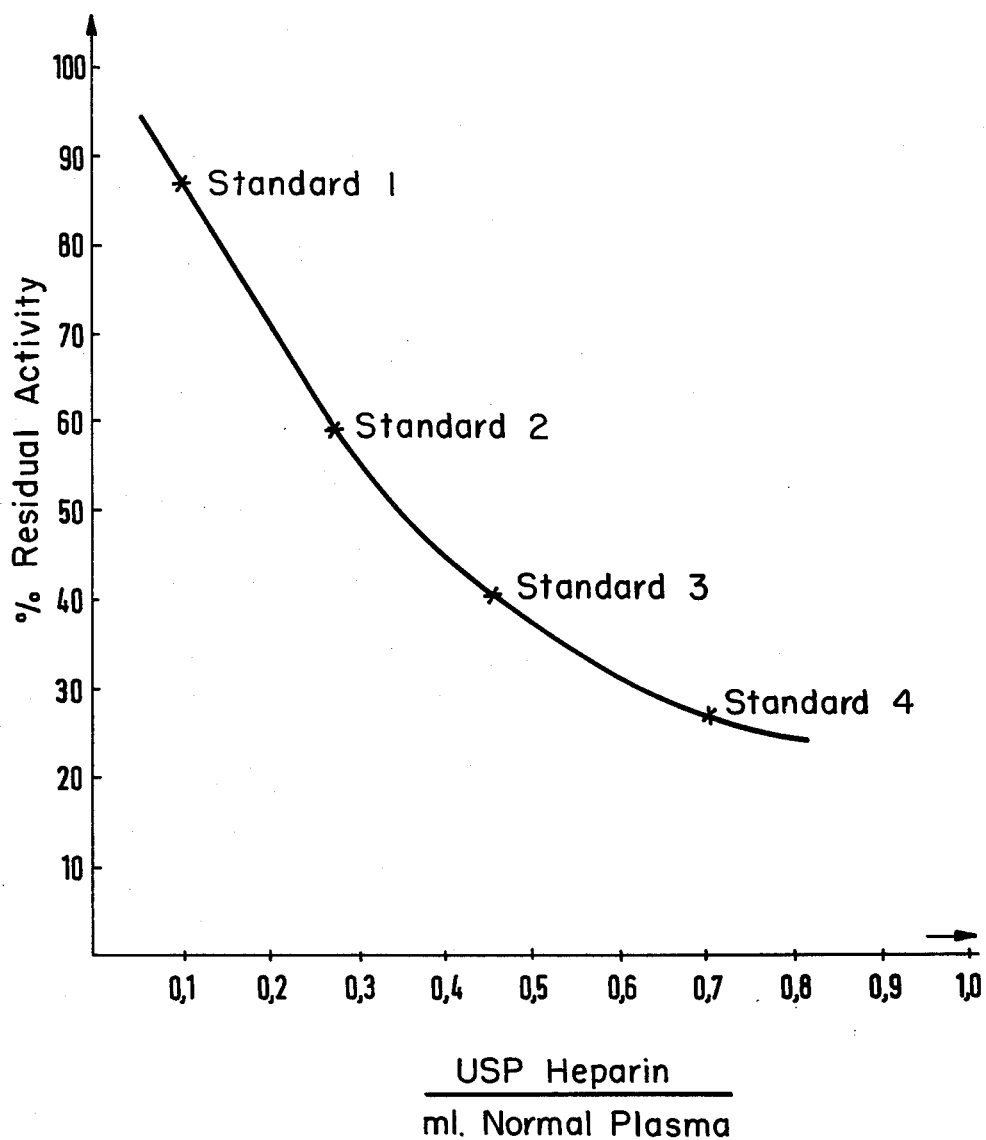

CONTROL REAGENT FOR HEPARIN ACTIVITY DETERMINATION

The invention relates to a control reagent for the determination of heparin activity (heparin standard) which is suited for standardization in the determination of biologically active heparin in plasma.

The determination of the biological activity of heparin represents an important parameter for monitoring the progress of a heparin therapy. In the method described in German patent application DOS No. 28 12 943, it is performed by measuring the inhibiting effect of the heparin/antithrombin III (AT III) complex on thrombin. For this commercial method of determination, it is important that it be suited for use with the various automatic analyzers available to research laboratories. For a number of reasons it is advantageous to evaluate the test by the use of a standard curve.

One of these reasons is that some of the parameters of measurement, such as incubation time, dosage volumes, etc., which are preset on automatic analyzers and are not variable, result in different inhibitory values or residual thrombin activities being obtained for the same sample on the various automatic analyzers. This means that different therapeutic ranges would have to be specified for the various automatic methods and the manual method, which is not feasible in practice.

Another reason is that the level of the residual thrombin activity is dependent in part on the initial thrombin value. The latter may vary as a function of production, and this, too, would affect the accuracy of measurement adversely. Since it is extremely important that the heparin concentration be adjusted precisely, both because of the hazard of thrombosis and because of the danger of the patient's bleeding to death, even minor analytical errors of the type mentioned may have serious consequences and may even result in the patient's death. Analytical errors of this type may be prevented by the use of standards.

The known methods of monitoring heparin therapy only determine the concentration of heparin in the plasma in the presence of an excess of AT III. For this reason, only aqueous heparin solutions which prior to the performance of the test are added to a standardized normal plasma in the presence of an excess of AT III are used in the preparation of the standards here employed.

Other known and commercially available standardized plasmas for activity determination of clotting parameters contain only AT III (without heparin), which renders them unsuited for use in test systems which determine the inhibiting effect of the heparin/AT III complex on thrombin. Moreover, for various reasons such control plasmas do not satisfy the conditions which a standard to be employed with this system must meet, the stability of control plasmas after reconstitution being limited to from one to two days at 4° C. Another problem encountered in the use of control plasmas for standardization is that here a relatively wide spread (2s range) is given for the required value. For standardization, however, and especially in heparin activity determination, the required value must be specified exactly, with but a very narrow spread, since even minor errors in measurement due to incorrect standardization can have serious consequences in the clinic.

It is thus the object of the invention to provide a stable control reagent (heparin standard) which is suited for use in monitoring a heparin therapy by means of determination of the biological activity of the heparin. Since the reagent is to be suitable for the construction of a standard curve, it is not enough to stay within a given spread for the heparin activity. Rather the required value, once determined and standardized, should remain absolutely constant over the period of stability indicated, that is to say, the storability must meet exacting requirements.

In accordance with the invention, this object is accomplished by a control reagent for heparin activity determination which is characterized in that it contains or consists of 20 to 1500 USP heparin,
2000 to 30000 IU antithrombin III,
0.15 to 1.5 millimoles serum albumin,
0.005 to 0.05 mole ethylenediaminetetraacetic acid sodium salt,
0 to 0.4 mole saccharose,
2000 to 20000 U aprotinin, and
buffer substance, pH 6.5 to 7.5, in dissolved or lyophilized form, based on the amount required to prepare 1 liter of solution.

By the use of specific amounts of heparin and/or AT III, an inhibitory value is standardized which corresponds to a specific amounts of heparin in normal plasma.

Surprisingly, it is possible in accordance with the invention to obtain a very stable heparin standard containing antithrombin III. While antithrombin III is termed "relatively stable" (Methods of Enzymology, vol. 45, B, Ed. Lorand, 653 [1976]), that stability falls far short of meeting the aforesaid requirements with respect to the stability of standards suited for monitoring heparin therapy. The standard in accordance with the invention, on the other hand, with 40% inhibition, for example, which corresponds to 0.3 USP heparin/ml normal plasma, even after 3 weeks' storage at 33° C. is stable for another 4 weeks at −20° C., and then for another 7 days at 4° C., that is to say, its inhibitory value varies from the initial value by less than 5%.

Additional stability data of standards in accordance with the invention with different inhibitory values are presented in the table given with the examples.

Since in the test system according to German patent application DOS No. 28 12 943, for which the standard in accordance with the invention is primarily intended, the activity of heparin is determined in percent of inhibiting or residual activity based on the thrombin used, with this standard, in contrast to the known standard or control plasmas, the concentrations of the various parameters of measurement for heparin and AT III are not given; instead, the amount of heparin which corresponds to the standardized residual thrombin activity in pooled normal plasma (normal AT III content) is given. This residual activity can be obtained by varying the heparin and/or AT III concentration. However, since this inhibitory value reflects even slight variations in heparin and/or AT III with extraordinary sensitivity, the prolonged stability is all the more surprising. An AT III lyophilizate purified by known processes and having a pronounced affinity for heparin is advantageously used as AT III. Commercially available heparin preparations may be used as sources of heparin.

Suitable buffer substances are those which are effective in the pH range indicated. The concentration advantageously ranges from 1 to 300 millimoles per liter, and preferably from 1 to 10 millimoles per liter. Preferred buffer substances are tris, citrate and phosphate.

The surprisingly high stability of the standard in accordance with the invention is obtained only when all constituents are present in the amounts specified. In a preferred composition, the reagent contains, on the basis of 1 liter of solution, 0.8 to 1.0 millimole bovine serum albumin, 0.009 to 0.011 mole ethylenediaminetetraacetic acid sodium salt, 0.03 to 0.05 mole saccharose, 8000 to 12000 U aprotinin, and buffer substance, pH 6.9 to 7.1.

The reagent in accordance with the invention makes it possible to perform the determination of the biological activity of heparin by the use of the test system according to German patent application DOS No. 28 12 943 conveniently either manually or with the various automatic analyzers. With the standard for determination of heparin activity in accordance with the invention it is not necessary, in contrast to prior-art standards for determination of heparin concentration, to use the heparin preparation employed in therapy also in the preparation of the standard, because of differences in activity. The feasibility of routine tests thus is greatly enhanced.

EXAMPLES 1 to 4

Four standards in accordance with the invention contained 0.88 millimole/liter bovine serum albumin, 0.01 mole/liter ethylenediaminetetraacetic acid sodium salt and 0.04 mole/liter saccharose, 10000 U/liter aprotinin and 2 millimoles/liter tris buffer, pH 7.0, each. The table which follows gives the amounts to heparin and antithrombin III used to obtain the different inhibitory values shown. The amounts of these substances needed to obtain the desired inhibitory value depend, in accordance with their activity, also on the parameters of the test system for which they are intended, for example, the initial thrombin value.

TABLE

| | RESIDUAL THROMBIN ACTIVITY (%) | | | |
|---|---|---|---|---|
| | Example 1 | Example 2 | Example 3 | Example 4 |
| AT III | 10 U/ml | 10 U/ml | 10 U/ml | U/ml |
| Heparin | 0.06 USP/ml | 0.28 USP/ml | 0.5 USP/ml | 0.8 USP/ml |
| Lyophilizate, intial value | 86.6 | 59.2 | 40.6 | 27.2 |
| Lyophilizate, dissolved, 7 days at +4° C. | 87.0 | 61.1 | 42.0 | 28.3 |
| Lyophilizate, stored 3 weeks at 33° C. | 86.6 | 59.1 | 40.1 | 24.6 |
| Lyophilizate, dissolved, stored 7 days at +4° C. | 86.6 | 61.9 | 42.2 | 26.6 |
| Lyophilizate, dissolved, stored 28 days at −20° C. | 86.7 | 59.5 | 40.0 | 25.1 |
| Lyophilizate, stored 28 days at −20° C. 7 days at +4° C. | 87.3 | 60.9 | 42.9 | 27.0 |

The standard curve obtained with the standards of examples 1 to 4 is shown in the accompanying drawing.

It will be understood that the specification and examples are illustrative but not limitative of the present invention and that other embodiments within the spirit and scope of the invention will suggest themselves to those skilled in the art.

What is claimed is:

1. A control reagent for heparin activity determination comprising 20 to 1500 USP heparin, 2000 to 30000 IU antithrombin III, 0.15 to 1.5 to millimoles serum albumin, 0.005 to 0.05 mole ethylenediaminetetraacetic acid sodium salt, 0 to 0.4 mole saccharose, 2000 to 20000 U aprotinin, and buffer substance, pH 6.5 to 7.5, per liter of control reagent solution.

2. Control reagent as claimed in claim 1 in dissolved form.

3. Control reagent as claimed in claim 1 in lyophilized form.

4. Control reagent as claimed in claim 1 comprising 0.8 to 1.0 millimole bovine serum albumin, 0.009 to 0.011 mole ethylenediaminetetraacetic acid sodium salt, 0.03 to 0.05 mole saccharose, 8000 to 12000 U aprotinin, and buffer substance, pH 6.9 to 7.1.

* * * * *